United States Patent [19]

Dexter et al.

[11] Patent Number: 4,973,559

[45] Date of Patent: Nov. 27, 1990

[54] CELLULOLYTIC, $N_2$-FIXING BACTERIA AND USE THEREOF

[75] Inventors: Lee B. Dexter, Princeville; John M. Gould, Brimfield, both of Ill.

[73] Assignee: The United States of America as represented by the Secretary of the Agriculture, Washington, D.C.

[21] Appl. No.: 462,928

[22] Filed: Jan. 12, 1990

Related U.S. Application Data

[63] Continuation of Ser. No. 139,559, Dec. 30, 1987, abandoned.

[51] Int. Cl.$^5$ .................. C12N 1/22; C12P 39/00; C12P 1/02; C12R 1/01
[52] U.S. Cl. ............................ 435/252; 435/42; 435/165; 435/171; 435/172.1; 435/252.4; 435/252.5; 435/252.7; 435/261; 435/822; 435/832; 435/842
[58] Field of Search .............. 435/42, 165, 171, 172.1, 435/252.4, 261, 252, 842, 252.7, 252.6, 822

[56] References Cited

U.S. PATENT DOCUMENTS

| | | | |
|---|---|---|---|
| 3,778,349 | 12/1973 | Carta . | |
| 4,306,027 | 12/1981 | Alexander et al. | 435/172.1 |
| 4,370,351 | 1/1983 | Harper | 435/804 |
| 4,421,544 | 12/1983 | Jones et al. | 435/253 |
| 4,643,899 | 2/1987 | Kerr et al. | 426/2 |
| 4,649,113 | 3/1987 | Gould | 435/165 |

FOREIGN PATENT DOCUMENTS 569497  1/1959  Canada ................ 435/253

OTHER PUBLICATIONS

Derwent Abstract, 85-274691/44, Berestetsk et al., SU 1151533, (4-85).
Derwent Abstract, 83-848658/51, Rubenchik, SU 239707, (8-1969).
Derwent Abstract, 80-332020c/19, Grenet, FR 2431998, (3-1980).
Biotech Abs. 88-00282, SU 1210383, (2-1987).
Derwent Abstract 88-061063/09, Kimura, J 63017283, (1-88).
Derwent Abs., 87-251904/36, Thierry et al., FR 2593171, (7-1987).
Derwent Abs., 81-87596D/48, Grenet, EP-40110, (11-1981).
Derwent Abs., 86-093225/14, Patyka et al., SU 1180366, (9-1985).
Derwent Abs., 87-081687/12, Barthes, FR 2586015, (2-1987).
Derwent Abs., 86-093225/14, Patyka et al., SU 1180366, (9-1985).
Derwent Abs., 87-262132/37, Vasyuk et al., SU 1210383, (2-87).
Derwent Abs., 85-217439/36, Hoflich et al., DD-222299, (5-1985).
John B. Waterbury et al., "A Cellulolytic Nitrogen-Fixing Bacterium Cultured from the Gland of Deshayes in Shipworms (Bivalvia: Teredinidae)," Science, 221:1401-1403, (Sep. 1983).
Duncan A. Veal et al. (I), "Biochemistry of Cellulose Breakdown by Mixed Cultures," Biochem. Soc. Trans., 12:1142-1144, (1984).
Duncan A. Veal et al. (II), "Associative Cellulolysis and $N_2$-Fixation by Co-Cultures of *Trichoderma harzianum* and *Clostridium butyricum*: The Effects of Ammonium-N on These Processes," *J. Appl. Bacteriol.*, 63:245-253, (1987).
Stephen H. T. Harper et al., "Dinitrogen Fixation by Obligate and Facultative Anaerobic Bacteria in Association with Cellulolytic Fungi," Curr. Microbiol., 14:127-131, (1986).
..., "A Treatise on Dinitrogen Fixation," Section III: Biology, R. W. F. Hardy, ed., John Wiley & Sons, New York, pp. 153, 159, (1979).
..., "A Treatise on Dinitrogen Fixation," Sections I & II: Inorganic and Physical Chemistry and Biochemistry, R. W. F. Hardy, ed., John Wiley & Sons, New York, pp. 653, 655, (1979).
..., "Nitrogen Fixation by Free-Living Micro-Organisms," W. D. P. Stewart, ed., Cambridge University Press, Cambridge, England, pp. 3-4, (1975).
H. Dalton, Methods for Evaluating Biological Nitrogen Fixation, F. J. Bergersen, ed., John Wiley & Sons, Ltd., pp. 13-14, (1980).
Richard V. Greene et al., "Growth Characteristics of a Novel Nitrogen-Fixing Cellulolytic Bacterium," Appl. Environ. Microbiol., 52(5):982-986, (Nov. 1986).

*Primary Examiner*—Herbert J. Lilling
*Attorney, Agent, or Firm*—M. Howard Silverstein; Curtis P. Ribando; John D. Fado

[57] ABSTRACT

Cellulolytic, $N_2$-fixing bacteria have been isolated from terrestrial ecosystems. Many of these bacteria can be taxonomically classified as Bacilli, while others may not be characteristic of any previously defined taxon. These organisms are useful for converting lignocellulosic and other cellulosic materials into foods and fertilizers having increased carbohydrate digestibility and enhanced assimilable nitrogen content.

3 Claims, No Drawings

CELLULOLYTIC, N$_2$-FIXING BACTERIA AND USE THEREOF

This application is a continuation of application Ser. No. 07/139,559, filed Dec. 30, 1987, now abandoned.

BACKGROUND OF THE INVENTION

1. Field of the Invention

Cellulose constitutes approximately 40% of the $1.8 \times 10^{12}$ tons of this planet's annual production of photosynthetically-generated material [R. H. Whittaker, *Communities and Ecosystems*, MacMillan, N. Y. (1970)]. For the most part, cellulose is bound in the form of lignocellulosic biomass, degradation of which is responsible for the vast majority of carbon recycled through the biosphere. Industrial sources of lignocellulose which feed this recycle stream include forestry byproducts, agricultural crop residues and byproducts, and municipal wastes. It has been observed by Veal et al. [Nature 310: 695–697 (Aug. 23, 1984)] that decomposition of the cellulose and hemicellulose is inhibited by a nitrogen limitation, and that this inhibition could be overcome by decomposer organisms which combined both cellulolytic and N$_2$-fixing functions.

2. Description of the Prior Art

The only single organism known to be reported in the literature possessing the combination of cellulolytic and N$_2$-fixing capabilities is a bacterium present in a gland in shipworms. This organism, originally discovered by J. D. Popham and M. R. Dickson [Marine Biol., 19: 338–340 (1973)] was first cultured in pure form by J. B. Waterbury et al. [Science 221: 1401–1403 (Sept. 1983)]. The bacterium isolated by Waterbury et al. is obligately marine, requiring high concentrations of Na$^+$, Cl$^-$, Mg$^{2+}$, and Ca$^{2+}$ for growth. Under aerobic conditions it requires a source of combined nitrogen, but when grown under microaerophilic conditions, it will fix molecular nitrogen.

Veal et al. [Biochem. Soc. Trans. 12: 1142–1144 (1984)] confirm that the shipworm bacterium is the only known organism capable of both cellulolysis and N$_2$-fixation. Veal et al. further report that the occurrence of these functions in other systems is the result of mixed species. For example, Harper et al [J. Appl. Bacteriol. 57: 131–137 (1984)] have isolated from decomposing straw aerobic fungi principally responsible for cellulolysis and anaerobic Clostridia responsible for N$_2$-fixation. Experiments conducted by Veal et al using *Trichoderma harzianum* and *Clostridium butyricum* verify this association, wherein the aerobe presumably provides respiratory protection to the anaerobe.

Several other cellulolytic fungi, including species of Fusarium, Penicillium, and Sordaria, were demonstrated by Harper et al. [Curr. Microbiol. 14: 127–131 (1986)] to associate with four different strains of *C. butyricum* in the same manner as *T. harzianum* in the decomposition of wheat straw.

These findings support the premise that communities exist in the terrestrial environment for biodegradation of cellulosic material. They also establish that certain of these communities can be cultivated in vitro, suggesting the feasibility of industrial fermentation processes for converting cellulose to more useful, nitrogen-containing end products. Of course, the success of such processes would depend largely on maintaining the appropriate balance between the respective organisms. Therefore, the advantages of discovering a single organism for this purpose would be readily apparent.

SUMMARY OF THE INVENTION

We have now unexpectedly discovered and for the first time isolated from a terrestrial environment microorganisms that are both cellulolytic and N$_2$-fixing. These organisms are the first nonmarine organisms known to be reported which have the ability to both degrade cellulosic materials and to fix atmospheric nitrogen. This invention therefore finds application in converting cellulosic waste to a product having increased carbohydrate digestibility and enhanced assimilable nitrogen content. Such products would be useful as food or food components for higher organisms such as plants, animals, and humans.

In accordance with this discovery, it is an object of the invention to provide isolated, free-living cultures of cellulolytic, N$_2$-fixing organisms.

It is also an object of the invention to utilize the subject organisms for the purpose of rendering crop residues, agricultural byproducts, wood, municipal wastes, and other forms of cellulosic materials into more useful forms.

It is another object of the invention to use microbial fermentation to upgrade the nitrogen content of materials which are conventionally amended with exogenous nitrogen for utilization as feeds and fertilizer.

Other objects and advantages of this invention will become readily apparent from the ensuing description.

DETAILED DESCRIPTION OF THE INVENTION

In reference to the organisms contemplated for use herein, the terms "nonmarine" and "nonobligate-marine" are intended to distinguish such organisms from their counterparts found in a marine or marine-like environment, and thereby requiring a cultivation medium having a high salt concentration similar to that found in seawater. The organisms of this invention are essentially terrestrial in the sense that they are naturally found in land or fresh water ecosystems. Thus the term "terrestrial" can also be applied to these organisms in accordance with the above definition.

The term "free-living" in relation to the subject organisms is intended to denote the property of existing on a cellulosic substrate or suitable cultivation medium independent from any other living organism. This term is not, however, intended to preempt the mutual presence of more than one isolate or strain of organism within the scope of this invention. Similarly, the term "isolate" in both its noun and verb forms, and derivatives thereof, are meant to encompass both the isolation of a single strain of cellulolytic, N$_2$-fixing organism, as well as a plurality of such strains apart from other microbial strains which are not so characterized.

"Cellulolytic" is used in its normal sense in reference to the property of degrading cellulose to shorter chain polysaccharides, oligosaccharides, dextrins or sugars. "N$_2$-fixing" refers to the property of fixing atmospheric nitrogen; that is, reducing molecular nitrogen (N$_2$) to ammonia, with or without further conversion of the ammonia to some inorganic or organic nitrogenous compound which can be assimilated by a higher life form. The end product of this process is referred to as "fixed nitrogen."

The subject organisms are found growing on cellulosic substrates in a great diversity of terrestrial environments. The term "cellulosic" means containing cellulose as an integral component, either in pure form or in conjunction with other materials, such as hemicellulose, xylan, or lignin. The organisms, for example, may be isolated from fallen leaves and trees, acorns, crop residues, plants, seed hulls, grass clippings, soils, insects, fungi, etc. We have found that preferred sources of these bacteria are environmental niches or microenvironments wherein decomposition of organic plant matter is occurring in the presence of low levels of fixed nitrogen. Bogs, marshes, acidic soils, leached cellulosic litters, herbivorous insects, and the surfaces of many of the aforementioned plant and crop residues are examples of such places.

The subject microorganisms are readily isolated from these materials on a selective nitrogen-deficient medium in which cellulose is the sole carbon source. By "nitrogen-deficient," it is meant that assimilable nitrogen is either totally absent or else present in an amount insufficient to sustain growth of nonnitrogen-fixing organisms. Without desiring to be limited thereto, a suitable medium for this purpose is Medium B described in Table I, below. In that it is not uncommon, as previously mentioned, for more than one strain to be found on a given substrate, pure isolates may be obtained by subculturing colonies from the selective medium.

Strains having the desired combination of cellulolytic and $N_2$-fixing characteristics can also be selected by sequential passage on both a nitrogen-deficient medium and a medium wherein the sole carbon source is cellulose. The nitrogen-deficient medium will of course select for the $N_2$-fixing strains, and the cellulosic medium for the cellulolytic strains. While the sequential order of passaging is not critical, it is preferred to first screen for the $N_2$-fixers in order to minimize the possibility that other cellulolytic populations would flourish at their expense. In fact, we have found that the organisms of the invention grow and compete most favorably against other populations when initially transferred from the environment to a nitrogen-deficient growth medium wherein the carbon source is a chemically degraded lignocellulosic material. An example of such a material is the alkaline peroxide-treated (AHP) wheat straw used as the carbon source in Medium A of Table I. This material was prepared by the method of Gould, U.S. Pat. No. 4,649,113 (herein incorporated by reference), as discussed further below. It is therefore preferred to use Medium A as an initial growth medium and Medium B as the selection medium.

Lignocellulosic substrates such as the AHP wheat straw of Medium A would theoretically not permit selection amongst organisms which are strictly ligninolytic or which are capable of degrading some of the other minor components of lignocellulosic materials. However, we have observed that Medium A, and certain media containing raw lignocellulosic materials as the sole carbon source, are nearly as effective as purified cellulose in selecting for cellulolytic organisms.

The practice of repeated serial transferring of the culture on initial growth and/or selection media reduces the possibility of contamination in the final culture by any population which is not both cellulolytic and $N_2$-fixing. A final check against such contaminants may be conducted by plating out the culture and passaging candidate colonies through the selective media. This plating is also useful for producing isolates where multiple strains of the subject bacteria are present in the selected culture.

Using the combination of Medium A and Medium B, described in Table I, and following the protocol set forth in Example 1, more than 180 bacterial strains within the scope of the invention have thus far been isolated. Thus, it has become quite evident that the person in the art applying the disclosed selection technique and media to a cellulosic substrate as defined above could readily isolate therefrom a bacterium having the cellulolytic, $N_2$-fixing properties necessary for carrying out the conversion process described below. Notwithstanding the apparent ubiquity of these bacteria in environments comprising decaying cellulosic materials, their heretofore obscurity is believed to be the result of their usual coexistence with a relatively large number of other organisms which have a role in the decomposition process. It is envisioned that other media similar to Medium A and Medium B in Table I could be applied in isolating organisms within the scope of the invention.

Based upon characterizations completed at the time of filing this application, the strains isolated by this inventive process have been categorized into three groups: Group I constituting approximately 144 isolates comprises organisms generally similar to each other but which are not appropriately classified in any of the known taxonomic genera; Group II constituting approximately 30 isolates comprises new strains or even new species of the genus Bacillus; and Group III constituting approximately 12 isolates which have not been sufficiently characterized to be taxonomically classified. The taxonomic characteristics of Groups I and II are as follows:

Group I gram (−)
elliptical rods
pleomorphic
motile by polar flagella
facultative anaerobes
no resting stages
grow in nitrogen-deficient media
utilize cellulose as a sole carbon source Group II gram (+)
long, slender rods
spore-formers
motile by peritrichous flagella
facultative anaerobes
grow in nitrogen-deficient media
utilize cellulose as sole carbon source By cultivating isolates obtained from the selective media under a variety of conditions and on a variety of transfer media, vigorous, nonfastidious strains can be isolated.

Organisms isolated in accordance with the aforementioned process are useful in the conversion of cellulosic materials to more useable forms. Examples of such materials can be categorized as follows:

Category I

Leaves and stalks of nonwoody plants, particularly monocotyledenous plants, and especially grassy species belonging to the family Gramineae. Of primary interest in this category are gramineous agricultural (crop) residues; that is, the portions of grain-bearing grassy plants which remain after harvesting the seed. Illustrative of such residues without limitation thereto are wheat straw, oat straw, rice straw, barley straw, rye straw, buckwheat straw, corn stalks, and the like. Also included within this category are certain grasses not conventionally cultivated for agricultural purposes, such as prairie grasses, gamagrass, and foxtail.

The term "woody" is used herein in the botanical sense to mean "comprising wood," that is, composed of extensive xylem tissue as found in trees and shrubs, and also in the sense of being woodlike. Accordingly, "nonwoody" refers to materials lacking these characteristics.

Category II

Agricultural byproducts including fruits, roots, tubers and components thereof. The terms "fruits," "roots," and "tubers" are used herein in the botanical sense. The lignocellulosic substrates of principal interest in this category are waste stream components from commercial processing of crop materials such as sugar beet pulp, citrus fruit pulp, nonwoody seed hulls, corn cobs, corn husks, and cereal bran. The term "citrus fruit pulp" defines the waste product of the citrus juice industry. This product typically includes both the rind of the fruit and also the fleshy juice sacs. The fleshy material is oftentimes also referred to as "pulp," and it alone is a suitable substrate within the ambit of the invention.

Category III

Forestry products and byproducts from deciduous and coniferous trees including bark, twigs, leaves, woodchips, sawdust, wood pulp, processed cellulose such as newsprint, etc.

Category IV

Miscellaneous, to include municipal waste and other sources of cellulose not within the scope of Categories I to III, above.

In preparation for microbial treatment in accordance with the method of the invention, the material may optionally be subjected to one or more preparatory steps such as chopping or grinding to facilitate handling or to enhance the surface-to-volume ratio. In some cases, it may be necessary to clean the substrate by screening, washing, or the like in order to remove dirt, debris, and other undesirable matter.

In addition, it may be desirable to pretreat the material by the AHP treatment described by Gould, supra. Despite the fact that Gould is limited to the treatment of nonwoody leaves and stalks as within Category I, above, for purposes of this invention materials within all of Categories I to IV could be advantageously treated, but especially those materials within Categories I and II.

Briefly, the Gould reaction is conducted in an aqueous medium in sufficient quantity to effect uniform wetting of the substrate with a peroxide to substrate ratio of at least about 0.01 (w/w). For optimum yield of available carbohydrate, the pH of the resultant slurry is controlled within the range of about 11.2 to about 11.8, and preferably as close to 11.5 as possible. Initial adjustment of the slurry pH to within the aforementioned range is readily accomplished by addition of sodium hydroxide or other strong alkali. The reaction of the alkaline peroxide with the lignocellulosic substrate proceeds at a relatively rapid rate at room temperature (25° C.).

The mechanism of $N_2$-fixation by the organisms of this invention is presumed to be akin to that of most other known $N_2$-fixers. Molecular nitrogen from the atmosphere is first reduced intracellularly in the nitrogenase system to ammonia. The ammonia is thereafter available to the organism for conversion into amino acids with subsequent assimilation into microbial protein. Alternatively, ammonia released from the cell may be converted by nitrification to nitrites and then to nitrates, and thereby become available for assimilation by plants. Other microorganisms introduced or naturally associated with the cellulose may also be instrumental in converting the fixed nitrogen to a product having nutritive value to higher organisms.

The substrate to be treated may be inoculated in situ as in the case of field crop residues. The fixed nitrogen thereby becomes available in the soil through the above-described process for utilization by a subsequent crop. In another embodiment, the material may be treated in a processing facility, wherein the nitrogen-enriched product would be recovered by appropriate means and then transported to its end use site.

The products of the invention are useful as fertilizer, feed for nonruminant animals such as fish, shellfish, or other aquatic organisms, ruminant animals such as cattle or sheep, and as a value-added dietary fiber for humans. When used as a feed component for livestock or aquatic animals, the inoculated cellulose substrate may be fermented in the holding pens, and thereby be directly available to the animal on an ad libitum basis.

The following examples are intended only to further illustrate the invention and are not intended to limit the scope of the invention, which is defined by the claims.

EXAMPLE 1

General Isolation Methodology for Cellulolytic, $N_2$-Fixing Bacteria

A small sample (approximately 0.5 g) of material collected from a microenvironment judged likely to contain $N_2$-fixing, cellulolytic bacteria was placed in a sterile 250-ml Erlenmeyer flask containing 100 ml of Medium A (Table I). Some environmental samples (e.g., insects) were first homogenized in a small amount of sterile Medium A in a Waring blender, and about 2 ml of the homogenate was used as the inoculum. For each environmental sample, three flasks were inoculated. Two were incubated without shaking (one at 28° C., one at 37° C.), and the third was incubated at 25° C. on a gyrorotary shaker operating at 100 rpm. Transfers were made into fresh Medium A (1 ml inocula into 100 ml medium) every 2 to 5 days (depending upon observed rate of growth) until five to seven transfers had occurred. At this point, sterile Erlenmeyer flasks containing 100 ml of Medium B were inoculated with 1 ml of the final Medium A culture exhibiting the best growth, and incubated under the same conditions. Transfers were made into fresh Medium B (1 ml inocula into 100 ml medium) every 2–5 days until five to seven transfers had been made. Isolation streak plates were then made from the final Medium B culture onto four different solid media: nutrient agar, brain heart infusion agar, mineral glucose agar, and no-nitrogen calcium chloride agar (Media C-F, respectively, Table II).

TABLE I

| | Amount (g/l tap water) | |
|---|---|---|
| Nutrient[a] | Medium A[b] | Medium B[b] |
| AHP-treated wheat straw[c] | 20 | — |
| purified alpha-cellulose[d] | — | 20 |
| $KH_2PO_4$ | 0.4 | 0.4 |
| $K_2HPO_4$ | 0.1 | 0.1 |

TABLE I-continued

| Nutrient[a] | Amount (g/l tap water) | |
|---|---|---|
| | Medium A[b] | Medium B[b] |
| $MgSO_4.7H_2O$ | 0.2 | 0.2 |
| NaCl | 0.1 | 0.1 |
| $CaCl_2$ | 0.02 | 0.02 |
| $FeCl_3$ | 0.01 | 0.01 |
| $NaMoO_4.2H_2O$ | 0.002 | 0.002 |
| "Difco" yeast extract | 0.05 | 0.05 |

[a]Medium adjusted to pH 7.3 ± 0.1.
[b]Modified ATCC Spirillum nitrogen-fixing medium No. 838.
[c]Alkaline hydrogen peroxide treated wheat straw ground to pass a 2-mm screen prepared by the method of Gould (U.S. Pat. No. 4,694,113).
[d]"Sigmacell" or "Solka-Floc SW-40".

Individual colonies growing on brain heart infusion agar, mineral glucose agar, and no-nitrogen calcium chloride agar were then replated onto nutrient agar. Based upon colony characteristics determined from comparison of individual colonies growing on all four types of solid media, the number of different organisms in the final Medium B liquid culture was determined, and each organism was assigned a unique number. Each individual organism was inoculated from nutrient agar plates into separate 250-ml Erlenmeyer flasks containing 100 ml of Medium A or 100 ml of Medium B, respectively. Transfers were made into fresh media (1 ml inocula into 100 ml medium) every 2-5 days until five to seven transfers had been made. Nutrient agar slants of isolates exhibiting good growth through these transfers on both Medium A and Medium B were established using the final Medium A liquid culture as the inoculum.

A number of the cellulolytic, $N_2$-fixing bacteria isolated by this procedure were subsequently characterized by standard methodologies. A summary of these bacteria and their taxonomic characterizations are reported below in Tables IIIA-IIIC. The collection sites of these and other cellulolytic, $N_2$-fixing organisms isolated by the procedure of Example 1 are summarized in Table IV.

The isolates constituting mixed cultures LD5 (LD5A-LD5C) and LD7 (LD7A-LD7L) were deposited under the Budapest Treaty with the Agricultural Research Service in Peoria, Ill. The NRRL Accession Numbers assigned to these isolates are summarized in Table V.

For purposes of illustration a more detailed description of the isolation and characterization of isolates LD5A-LD5C is given in Example 2 and accompanying Table VI, below.

TABLE II

| Media Formulations: | |
|---|---|
| Nutrient Agar (Medium C) | |
| beef extract | 3 g |
| peptone | 5 g |
| agar | 15 g |
| distilled $H_2O$ | 1 l |
| pH 6.8 ± 0.2 | |
| Brain Heart Infusion Agar (Medium D) | |
| calf brains infusion | 200 g |
| beef hearts infusion | 250 g |
| peptone | 10 g |
| glucose | 2 g |
| sodium chloride | 5 g |
| disodium phosphate | 2.5 g |
| agar | 15 g |
| distilled water | 1 l |
| pH 7.4 ± 0.2 | |
| No Nitrogen $CaCl_2$ Agar (Medium E) | |
| glucose | 20 g |

TABLE II-continued

| Media Formulations: | |
|---|---|
| $K_2HPO_4$ | 0.8 g |
| $KH_2PO_4$ | 0.2 g |
| $FeCl_3.6H_2O$ | 0.1 g |
| $MgSO_4.7H_2O$ | 0.5 g |
| $CaCl_2.2H_2O$ | 0.05 g |
| $NaMoO_4.2H_2O$ | 0.05 g |
| agar | 20 g |
| distilled $H_2O$ | 1 l |
| pH 7.4-7.6 | |
| Mineral Glucose Agar (Medium F) | |
| glucose | 20 g |
| $K_2HPO_4$ | 0.8 g |
| $KH_2PO_4$ | 0.2 g |
| $MgSO_4.7H_2O$ | 0.5 g |
| $FeCl_3.6H_2O$ | 0.1 g |
| $CaCO_3$ | 20 g |
| $Na_2MoO_4.2H_2O$ | 0.05 g |
| agar | 20 g |
| distilled $H_2O$ | 1 l |
| pH 7.4-7.6 | |
| No Nitrogen Liquid Becking Media (Medium G) | |
| glucose | 20 g |
| $K_2HPO_4$ | 0.8 g |
| $KH_2PO_4$ | 0.2 g |
| $MgSO_4.7H_2O$ | 0.5 g |
| $FeCl_3.6H_2O$ | 0.05 g |
| $CaCl_2.2H_2O$ | 0.05 g |
| $NaMoO_4.2H_2O$ | 0.05 g |
| distilled $H_2O$ | 1.0 l |
| pH 7.4-7.6 | |

TABLE IIIA

Group I Organisms
(Noncharacteristic of Known Taxonomic Groups)
These organisms have the following characteristics in common: gram negative, elliptical rods (often pleomorphic); motile, at least in early growth stages; those organisms examined exhibit one or two polar flagella; facultatively anaerobic; sustained growth through multiple transfers on each of the following media: Media A and B (modified ATCC Spirillum nitrogen-fixing medium); form gas from glucose; do not make $H_2S$ on triple-sugar iron agar[d]; no resting stages observed. G ± C (for those isolates tested = 60–73%. Additional characteristics for isolates used in Examples 2-19 are given below.

| Isolate | Oxidase[b] | Catalase[c] | Nitrate[e] | VP[e] |
|---|---|---|---|---|
| LD5B | − | + | − | − |
| LD5C | − | + | + | + |
| LD7A | − | + | − | − |
| LD7B | − | + | + | + |
| LD7C | − | − | + | − |
| LD7D | − | + | − | − |
| LD7E | − | + | + | − |
| LD7F | − | + | − | − |
| LD7G | − | + | − | − |
| LD7H | + | + | − | − |
| LD7I | − | − | − | − |
| LD7J | − | − | + | − |
| LD7K | − | + | − | + |
| LD10D | − | + | − | − |
| LD10E | − | − | + | − |
| LD10F | + | + | + | − |
| LD10G | − | + | − | − |
| LD10H | − | + | + | − |
| LD10I | − | + | − | − |
| LD10J | − | − | − | − |
| LD10K | + | − | − | − |
| LD10O | − | + | − | − |
| LD10P | − | − | − | − |
| LD10R | − | + | + | + |
| LD10S | − | − | − | − |
| LD10T | − | − | − | − |
| LD10U | − | + | − | − |
| LD10V | − | + | − | − |
| LD10Y | − | + | − | − |
| LD10AA | + | + | + | − |
| LD10BB | + | + | − | − |
| LD10CC | − | − | − | − |

TABLE IIIA-continued

Group I Organisms
(Noncharacteristic of Known Taxonomic Groups)
These organisms have the following characteristics in common:
gram negative, elliptical rods (often pleomorphic); motile, at least
in early growth stages; those organisms examined exhibit one or
two polar flagella; facultatively anaerobic; sustained growth
through multiple transfers on each of the following media: Media
A and B (modified ATCC Spirillum nitrogen-fixing medium); form gas
from glucose; do not make $H_2S$ on
triple-sugar iron agar[a]; no resting stages observed. G ± C (for
those isolates tested = 60–73%. Additional characteristics for
isolates used in Examples 2–19 are given below.

| Isolate | Oxidase[b] | Catalase[c] | Nitrate[e] | VP[e] |
|---|---|---|---|---|
| LD10DD | − | − | − | − |

[a]Difco Manual, 10th Edition, Difco Laboratories, Inc., Detroit, MI, pp. 1019–1020 (1984).
[b]Bailey and Scott's Diagnostic Microbiology, 7th Edition (S. M. Finegold and E. J. Baron, ed.), C. V. Mosby Co., St. Louis, MO, p. 113 (1986).
[c]Manual of Clinical Microbiology, 4th Edition (E. H. Lennette, A. Balows, W. J. Hauser, Jr., and H. J. Shadomy, eds.), American Society for Microbiology, Washington, D.C., p. 1093 (1985).
[d]R. E. Gordon, W. C. Haynes, C. H.-N. Pang, The Genus Bacillus, Agricultural Handbook No. 427, USDA, p. 12 (1973).
[e]Voges-Proskauer test, Difco Manual, supra, pp. 543–545.

TABLE IIIB

Group II Organisms (Characteristic of the Genus Bacillus)
These organisms have the following characteristics in common:
gram positive, long, slender rods; motile, at least in early
growth stages; those organisms examined exhibit peritrichous
flagella; facultatively anaerobic; sustained growth through
multiple transfers on each of the following media: Media A and
B (modified ATCC Spirillum nitrogen-fixing medium No. 838),
Medium F (mineral glucose agar), and Medium G (Becking
medium); do not make $H_2S$ on triple-sugar iron agar[a]; form
endospores in late growth stages. Additional characteristics for
isolates used in Examples 2–19 are given below.

| Isolate | Oxidase[b] | Catalase[c] | Nitrate[e] | VP |
|---|---|---|---|---|
| LD5A | + | + | + | − |
| LD7L | + | + | − | − |
| LD10B | + | + | − | − |
| LD10C | − | − | − | − |
| LD10L | + | + | + | − |
| LD10M | − | − | − | − |
| LD10N | − | + | − | − |
| LD10Q | − | + | − | − |
| LD10W | − | + | − | − |
| LD10X | − | + | − | − |
| LD10Z | + | + | + | + |

[a]Difco Manula, 10th Edition, Difco Laboratories, Inc., Detroit, MI, pp. 1019–1020 (1984).
[b]Bailey and Scott's Diagnostic Microbiology, 7th Edition (S. M. Finegold and E. J. Baron, ed.), C. V. Mosby Co., St. Louis, MO, p. 113 (1986).
[c]Manual of Clinical Microbiology, 4th Edition (E. H. Lennette, A. Balows, W. J. Hauser, Jr., and H. J. Shadomy, eds.), American Society for Microbiology, Washington, D.C., p. 1093 (1985).
[d]R. E. Gordon, W. C. Haynes, C. H.-N. Pang, The Genus Bacillus, Agricultural Handbook No. 427, USDA, p. 12 (1973).
[e]Voges-Proskauer test, Difco Manual, supra, pp. 543–545.

TABLE IIIC

Group III Isolates (not Taxonomically Characterized)
The Taxonomic characterization of the organisms listed below is
incomplete at this time. All organisms exhibit sustained growth
through multiple transfers on each of the following media: Media
A and B (modified ATCC Spirillum nitrogen-fixing medium
No. 838), Medium F (mineral glucose agar), and Medium G
(Becking medium).

| Isolate |
|---|
| LD10A |
| LD10N |
| LD10Q |
| LD10X |
| LD27A |
| LD27B |
| LD27C |

TABLE IIIC-continued

Group III Isolates (not Taxonomically Characterized)
The Taxonomic characterization of the organisms listed below is
incomplete at this time. All organisms exhibit sustained growth
through multiple transfers on each of the following media: Media
A and B (modified ATCC Spirillum nitrogen-fixing medium
No. 838), Medium F (mineral glucose agar), and Medium G
(Becking medium).

| Isolate |
|---|
| LD27D |
| LD27E |
| LD27F |
| LD27G |
| LD27H |
| LD27I |

TABLE IV

Sources of Cellulolytic, $N_2$-Fixing Bacteria

| Isolate No. | Collection site |
|---|---|
| LD1A–LD1H | Potato peel collected from pile of waste potates discarded onto a field in northern Peoria County, IL |
| ID2A–LD2I | Acorns collected from ground under a white oak tree (*Quercus alba*) in central Peoria County, IL |
| LD3A–LD3K | Unprocessed, whole grain rice organically grown in Louisiana |
| LD4A | Found growing in laboratory glassware containing distilled water and AHP-treated wheat straw, eastern Peoria County, IL |
| LD5A–LD5C | Cattail shoot collected from a glacial moraine, central Peoria County, IL |
| LD6A–LD6D | Corn stover collected from an agricultural field in central Peoria County, IL |
| LD7A–LD7L | Marsh soil at the base of a small glacial moraine, central Peoria County, IL |
| LD8A–LD8L | Bog soil, central Peoria County, IL |
| LD9A–LD9J | Bog soil, Kettle Moraine State Forest, Fondulac County, WI |
| LD10A–LD10DD | Oak root saprophyte (*Conopholis americana*) collected in Kettle Moraine State Forest, Sheboygan County, WI |
| LD11A–LD11E | Litter beneath a cedar tree (*Juniperus ashei*), central Travis County, TX |
| LD12A–LD12W | Common field grasshopper collected in central Peoria County, IL |
| LD14A–LD14Q | Ants (*Atta texana*) collected in western Bastrop County, TX |
| LD17A–LD17K | Discarded AHP-treated sugar cane bagasse, eastern Peoria County, IL |
| LD18A–LD18Q | Rotting wheat grain collected from inside wooden storage bin, central Peoria County, IL |
| LD27A–LD27I | Cypress swamp water, Cameron County, LA |
| LD77A–LD77F | Rotting wheat grain collected from inside wooden storage bin, central Peoria County, IL |

TABLE V

| Isolate | NRRL Accession No. |
|---|---|
| LD5A | B18270 |
| LD5B | B18271 |
| LD5C | B18272 |
| LD7A | B18273 |
| LD7B | B18274 |
| LD7C | B18275 |
| LD7D | B18276 |
| LD7E | B18277 |
| LD7F | B18278 |
| LD7G | B18279 |
| LD7H | B18280 |
| LD7I | B18281 |
| LD7J | B18282 |
| LD7K | B18283 |
| LD7L | B18284 |

TABLE VI

| Isolate | LD5A | LD5B | LD5C |
|---|---|---|---|
| Colony Characteristics on nutrient agar: | | | |
| media | nutrient agar | nutrient agar | nutrient agar |
| shape | irregular | round | round |
| surface | rough | smooth | smooth |
| margin | rhizoid | entire | undulated |
| elevation | raised | raised | umbonated |
| consistency | dry | viscid | butyrous |
| color | white | cream | clear |
| optical | opaque | translucent | translucent |
| Growth on solid media: | | | |
| mineral glucose agar | + | + | + |
| maconkey agar | − | + | + |
| endo agar | − | + | − |
| hektoen enteric agar | − | + | + |
| General characteristics: | | | |
| gram stain | + | − | − |
| morphology | long, slender rod | elliptical rod, pleomorphic | elliptical rod, pleomorphic |
| motile | + | + | + |
| flagella | peritrichous | polar | polar |
| $O_2$ requirement | facultative anaerobe | facultative anaerobe | facultative anaerobe |
| resting stage | spores | none | none |
| guaine + cytosine (mole percent) | 38.6 | 69.1 | n.d. |
| Biochemical characteristics: | | | |
| oxidase | + | − | − |
| catalase | + | + | + |
| nitrate | + | − | + |
| methyl red | + | − | + |
| Vogues-Proskauer | − (pH 5.7) | − | + |
| $H_2$ production | − | − | − |
| citrate | − | + | − |
| indole | − | − | + |
| urea | − | − | − |
| gas production | − | + | + |
| phenalanine utilization | − | − | − |
| ornithine utilization | − | −. | + |
| lysine utilization | − | − | − |
| arginine utilization | + | − | − |
| lysozyme tolerance | + | n.d. | n.d. |
| NaCl tolerance (%) | 0-7 | 0-10 | 0-7 |
| gelatin liquification | + | + | − |
| lipase | − | + | − |
| casein | + | − | − |
| esculin | + | + | + |
| DNase | + | + | + |
| eosin methylene blue (emb) | + | + | − |
| litmus milk | alkaline reaction, coagulation | n.d. | n.d. |
| crystalline dextrins | none | n.d. | n.d. |
| Oxidative growth: | | | |
| glucose | + | + | + |
| starch | + | + | + |
| lactose | + | + | + |
| maltose | + | + | + |
| sucrose | + | + | + |
| arabinose | − | + | + |
| fructose | + | + | + |
| xylose | + | + | + |
| mannitol | − | + | + |
| Fermentative growth: | | | |
| gluocose | + | + | + |
| starch | + | + | + |
| lactose | weak | + | + |
| maltose | weak | + | + |
| sucrose | + | + | + |
| arabinose | − | + | + |
| fructose | + | + | + |
| xylose | + | + | + |
| mannitol | − | + | + |

EXAMPLE 2

Isolation of Cellulolytic, $N_2$-Fixing Bacteria

Approximately 0.5 g of cattail shoot was placed in each of three sterile 250-ml Erlenmeyer flasks containing 100 ml of sterile Medium A. The cattail shoot sample was collected on Sept. 1, 1985, from the center stalk of an immature cattail plant (*Typha latifolia*) growing on a glacial moraine in central Peoria County, Ill. Two of the flasks were incubated without shaking (one at 28° C., one at 37° C.), and the third was incubated at 25° C. on a gyrorotary shaker operating at 100 rpm. Transfers were made into fresh Medium A (1 ml inocula into 100 ml medium) every 2 or 3 days until a total of five transfers had been made. At this point, sterile Erlenmeyer flasks containing 100 ml of Medium B were inoculated with 1 ml of the final Medium A culture grown at 28° C. without shaking, and incubated under the same conditions. Transfers were made into fresh Medium B (1 ml inocula into 100 ml medium) every 2 or 3 days until five transfers had been made. Isolation streak plates were then made from the final Medium B culture onto four different solid media: nutrient agar, brain heart infusion agar, mineral glucose agar, and no-nitrogen calcium chloride agar (Media C–F, respectively, Table II). Individual colonies growing on brain heart infusion agar, mineral glucose agar, and no-nitrogen calcium chloride agar were then replated onto nutrient agar. Based upon colony characteristics determined from comparison of individual colonies growing on all four types of solid media, it was determined that three different organisms were contained in the final Medium B liquid culture. These were designated as isolates LD5A, LD5B, and LD5C, respectively. Each of the isolates was inoculated from nutrient agar plates into separate 250-ml Erlenmeyer flasks containing 100 ml of Medium A or 100 ml of Medium B, respectively. Transfers were made into fresh media (1 ml inocula into 100 ml medium) every 2 or 3 days until five transfers had been made. Since all three isolates grew well in both Medium A and Medium B through the five transfers, pure cultures of each isolate were established and maintained on nutrient agar slants inoculated from the final Medium A liquid culture.

Detailed taxonomic characterizations of isolates LD5A-C are given in Table VI.

EXAMPLE 3

Protein Production by Organism LD5B Growing in a Nitrogen-Deficient Medium with Cellulose as Sole Carbon Source Liquid cultures of organism LD5B were grown in sterile 250-ml Erlenmeyer flasks containing 100 ml of Medium A or Medium B. The cultures were inoculated on day 0 with 1.0 ml of a 48-hr-old liquid culture of LD5B grown on Medium A, and incubated at 28° C. on a gyrorotary shaker operated at 90 rpm. After the indicated number of days, a 2.0-ml aliquot of the culture medium was removed and centrifuged at $12,500 \times g$ for 15 min to sediment cellulose particles and microbial cells. The protein content of the cell-free supernatant, determined by the method of Lowry [O. H. Lowry et al., J. Biol. Chem. 193: 265 (1951)], was <0.04 mg/ml. The pellet was resuspended in approximately 4.5 ml of deionized, distilled $H_2O$, centrifuged at $12,500 \times g$ for 15 min, and the resulting pellet resuspended in 1.0 ml of distilled, deionized $H_2O$. Duplicate 0.5-ml aliquots of the sample were added to 0.5 ml of 1N NaOH and incubated at 100° C. for 10 min to lyse the cells. After cooling, the protein content of the suspension was determined by the method of Lowry [supra], using bovine serum albumin as the standard. The results are reported in Table VII, below.

TABLE VII

Protein Production by Organism LD5B in Nitrogen-Deficient Media with Cellulose as Sole Carbon Source

| | Carbon source | |
|---|---|---|
| Day | AHP-treated wheat straw (Medium A) (mg protein/ml) | Wood pulp cellulose[a] (Medium B) (mg protein/ml) |
| 0 | <0.002 | <0.002 |
| 1 | 0.062 | 0.013 |
| 2 | 0.139 | n.d.[b] |
| 3 | 0.206 | 0.007 |
| 5 | 0.268 | n.d.[b] |
| 7 | 0.147 | 0.016 |

[a] "Solka-Floc SW-40."
[b] n.d. = not determined.

EXAMPLE 4

Protein Production by Mixed Cultures LD7 and LD10 in Nitrogen-Deficient Media Containing AHP-Treated Wheat Straw as Sole Carbon Source Mixed cultures LD7 (12 isolates, LD7A–LD7L) and LD10 (30 isolates, LD10A–LD10DD) were grown in sterile 250-ml Erlenmeyer flasks containing 100 ml of the Medium A. These flasks had been inoculated on day 0 with 1.0 ml of a 48-hr-old liquid culture grown on the same medium, and incubated at 28° C. without shaking. On the indicated day, the insoluble fraction of each culture was collected by centrifugation at $15,300 \times g$ for 20 min. The resulting pellet was resuspended in approximately 20 ml of distilled water and again centrifuged at $15,300 \times g$ for 20 min. The final pellet was dried at 50° C. for 24 hr, ground with a mortar and pestle, and the nitrogen content (in grams N per 100 g dry solids) determined with a "Leco" Carbon-Hydrogen-Nitrogen Analyzer. Protein content was taken as $6.25 \times N$ [D. Herbert et al., Methods in Microbiology, Academic Press, Vol. 5B, pp. 243–244 (1971)]. The results are reported in Table VIII, below.

TABLE VIII

Protein Production by Mixed Cultures LD7 and LD10 in Nitrogen-Deficient Media Containing AHP-Treated Wheat straw as Sole Carbon Source

| | Protein in Insoluble Fraction[a] | |
|---|---|---|
| Day | LD7[b] | LD10[c] |
| 0 | 0.63 | 0.63 |
| 1 | 0.81 | 0.94 |
| 2 | 1.00 | 1.06 |
| 3 | 2.69 | 1.44 |
| 4 | 2.50 | 1.38 |
| 7 | 2.06 | 1.88 |

[a] Grams protein per 100 g dry solids.
[b] Contained isolates LD7A–LD7L.
[c] Contained isolates LD10A–LD10DD.

EXAMPLES 5–8

Effect of AHP Treatment of Wheat Straw on Protein Production by Mixed Cultures LD7 and LD27 Growing in Nitrogen-Deficient Medium Flasks were inoculated with mixed cultures LD7 (12 isolates, LD7A–LD7L) and LD27 (9 isolates, LD27A–LD27I), and the cultures were grown as described in Example 4, except that for Examples 5 and 7 AHP-treated wheat straw was replaced with untreated wheat straw that had been ground in a Wiley mill to pass a 2-mm screen. The insoluble portion of each culture was collected, washed, and its protein content determined as described in Example 4. The results are reported in Table IX, below.

TABLE IX

Effect of AHP Treatment of Wheat Straw on Protein Production by Mixed Cultures LD7 and LD27 Growing in Nitrogen-Deficient Media

| Example | Mixed culture | Substrate | Protein in insoluble fraction[a] Day 0 | Day 7 | Increase (%) |
|---|---|---|---|---|---|
| 5 | LD7[b] | WS[c] | 2.13 | 2.94 | 38 |
| 6 | LD7[b] | AHP-WS[d] | 0.75 | 2.25 | 200 |
| 7 | LD27[e] | WS[c] | 1.88 | 2.44 | 30 |
| 8 | LD27[e] | AHP-WS[d] | 0.63 | 2.63 | 320 |

[a]Grams protein per 100 g dry solids.
[b]Contained organisms LD7A-LD7L.
[c]WS = wheat straw.
[d]AHP-WS = alkaline hydrogen peroxide treated wheat straw.
[e]Contained organisms LD27A-LD27I.

EXAMPLES 9–16

Protein Production by Mixed Culture LD27 Growing on Nitrogen-Deficient Medium Using Various Carbon Sources Flasks were inoculated with mixed culture LD27 (9 isolates, LD27A-LD27I), and the culture was grown as described in Example 4, replacing the AHP-treated wheat straw with various carbon sources (2 g/flask) as indicated. AHP treatments of the substrates were carried out as described by Gould [U.S. Pat. No. 4,694,113]. All substrates were ground in a Wiley mill to pass a 2-mm screen. Protein content (grams/100 g dry solids) of the insoluble fraction in each culture was determined as described in Example 4. The results are reported in Table X, below.

TABLE X

Protein Production by Mixed Cultrue LD27[a] Growing on Nitrogen-Deficient Media Using Various Carbon Sources

| Example | Substrate | Protein in insoluble fraction[b] Day 0 | Day 7 | Increase (%) |
|---|---|---|---|---|
| 9 | wheat straw | 1.88 | 2.44 | 30 |
| 10 | AHP-treated wheat straw | 0.63 | 2.63 | 320 |
| 11 | corn stover | 3.56 | 4.50 | 26 |
| 12 | AHP-treated corn stover | 1.13 | 2.69 | 139 |
| 13 | bagasse | 0.81 | 2.00 | 146 |
| 14 | AHP-treated bagasse | 1.25 | 2.56 | 105 |
| 15 | big bluestem | 1.0 | 2.25 | 125 |
| 16 | AHP-treated big bluestem | 0.62 | 1.50 | 140 |

[a]Contained organisms LD27A-LD27I.
[b]Grams protein per 100 g dry solids.

EXAMPLE 19

Live Weight Gain for Crayfish Fed a Balanced Crayfish Diet or AHP-Treated Wheat Straw Preincubated with Mixed Culture LD7

The feed value of AHP-treated wheat straw preincubated with mixed culture LD7 (12 isolates, LD7A-LD7L) was evaluated using juvenile white river crayfish (*Procambarus acutus*). Sterile 20-l carboys containing 10 l of the liquid growth Medium A amended with 1.5 g/l NH$_4$Cl were inoculated with 10 ml of a 48-hr-old liquid culture grown on the same medium. The carboys were incubated at 25° C. without shaking, but sterile air was bubbled through the medium to ensure adequate aeration and mixing of contents. Beginning after 2 to 3 days incubation, a portion of the solids was collected daily by filtration on a fine wire mesh screen, and was fed to crayfish as described below.

Crayfish having an initial weight of 1.5–4 g/animal were maintained in 5-gal glass aquaria with four animals per aquarium. Each aquarium contained continuously aerated tap water to a depth of about 6 cm and a small plastic shelter. Crayfish in one aquarium were fed wet microbially amended AHP-treated wheat straw equal to approximately 1% of their body weight at 0800 and 1600 hr daily. Crayfish in a separate aquarium were fed a similar level of a balanced, high-protein crayfish feed (Table XI) instead of the AHP-treated wheat straw. Crayfish from both aquaria were weighed periodically, and the average weight gain per animal calculated. The results are reported in Table XII, below.

TABLE XI

Composition of Balanced Crayfish Diet

| Ingredient | Percent (dry matter basis) |
|---|---|
| soybean meal | 40 |
| corn | 30 |
| wheat shorts | 15 |
| fish meal | 4 |
| vitamin premix[a] | 0.5 |
| mineral premix[a] | 4 |
| soybean oil | 4 |
| carboxymethyl cellulose | 2 |
| cholesterol | 0.5 |

[a]Vitamin and mineral premixes are the same as reported by Robinson et al. [Aquaculture 38: 145-154 (1984)].

TABLE XII

Live Weight Gain for Crayfish Fed a Balanced Crayfish Diet or AHP-Treated Wheat Straw Preincubated with Mixed Culture LD7

| Weeks | Cumulative live weight gain/animal (g) | |
|---|---|---|
| | LD7[a]-treated, AHP-treated wheat straw | Balanced diet[b] |
| 2 | 0.08 | −0.08 |
| 4 | 0.12 | 0.35 |
| 6 | 0.30 | 1.00 |
| 8 | 1.52 | 1.45 |

[a]Contained organisms LD7A-LD7L.
[b]See Table XI.

It is understood that the foregoing detailed description is given merely by way of illustration and that modification and variations may be made therein without departing from the spirit and scope of the invention.

We claim:

1. A free-living biologically pure culture of a terrestrial, cellulolytic, N$_2$-fixing, facultative anaerobic bacterium.

2. A biologically pure mixed culture free-living, terrestrial, cellulolytic, N$_2$-fixing, facultative anaerobic, bacterial isolates.

3. A fermentation broth comprising a cellulosic substrate and an inoculum consisting of one or more isolates of terrestrial, cellulolytic, N$_2$-fixing, facultative anaerobic bacteria.

* * * * *